(12) United States Patent
Katakura et al.

(10) Patent No.: US 9,014,517 B2
(45) Date of Patent: Apr. 21, 2015

(54) FIBER UNIT

(71) Applicant: Olympus Medical Systems Corp., Tokyo (JP)

(72) Inventors: Masahiro Katakura, Chofu (JP); Takeshi Suga, Hino (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 14/099,239

(22) Filed: Dec. 6, 2013

(65) Prior Publication Data

US 2014/0177266 A1  Jun. 26, 2014

Related U.S. Application Data

(63) Continuation of application No. PCT/JP2013/063168, filed on May 10, 2013.

(60) Provisional application No. 61/680,884, filed on Aug. 8, 2012.

(51) Int. Cl.
  *G02B 6/00* (2006.01)
  *A61B 1/00* (2006.01)
  *A61B 5/00* (2006.01)
  *G02B 6/02* (2006.01)

(52) U.S. Cl.
  CPC .............. *A61B 1/00165* (2013.01); *G02B 6/00* (2013.01); *A61B 5/0084* (2013.01); *G02B 6/02042* (2013.01)

(58) Field of Classification Search
  CPC ..... A61B 1/00165; A61B 5/0084; G02B 6/00
  USPC .............................. 385/12; 362/574
  See application file for complete search history.

(56) References Cited

U.S. PATENT DOCUMENTS 4,589,404 A * 5/1986 Barath et al. .................. 600/108
4,718,406 A * 1/1988 Bregman et al. .............. 600/130

(Continued)

FOREIGN PATENT DOCUMENTS

JP   A-63-8622        1/1988
JP   05341158 A  *   12/1993

(Continued)

OTHER PUBLICATIONS

International Search Report issued in International Patent Application No. PCT/JP2013/063168 dated Aug. 13, 2013.

*Primary Examiner* — Peter Radkowski
(74) *Attorney, Agent, or Firm* — Oliff PLC

(57) ABSTRACT

A fiber unit has an illumination fiber and detection fibers. The illumination fiber and the detection fiber comprise a soft portion that is bendable, a distal end hard portion provided at an end thereof and having a greater hardness than the soft portion, and a pitch conversion portion that connects the soft portion and the distal end hard portion and changes a distance between adjacent fibers at the distal end hard portion with respect to a distance between the adjacent fibers at the soft portion, by bending and extending. 1.0 degree<Deg_max<6.0 degrees, where Deg_max is a most inclined angle of angles each formed by a central axis of the distal end hard portion and a line segment connecting an end portion of the pitch conversion portion closer to the soft portion and an end portion of the pitch conversion portion closer the distal end hard portion.

6 Claims, 5 Drawing Sheets

(56) References Cited

U.S. PATENT DOCUMENTS

| | | | |
|---|---|---|---|
| 5,439,000 A * | 8/1995 | Gunderson et al. | 600/473 |
| 7,492,998 B2 * | 2/2009 | Miller et al. | 385/116 |
| 2001/0031115 A1 * | 10/2001 | Chen et al. | 385/54 |
| 2002/0007111 A1 * | 1/2002 | Deckert et al. | 600/177 |
| 2002/0013513 A1 * | 1/2002 | Bala | 600/178 |
| 2003/0191368 A1 * | 10/2003 | Wang et al. | 600/160 |
| 2006/0018031 A1 * | 1/2006 | Takasugi | 359/661 |
| 2006/0043636 A1 * | 3/2006 | Hsueh | 264/236 |
| 2006/0045444 A1 * | 3/2006 | Miller et al. | 385/115 |
| 2006/0052668 A1 * | 3/2006 | Homma | 600/177 |
| 2009/0299352 A1 * | 12/2009 | Zerfas et al. | 606/15 |
| 2010/0220293 A1 * | 9/2010 | Mizushima et al. | 353/20 |
| 2011/0137126 A1 * | 6/2011 | French et al. | 600/178 |
| 2011/0319874 A1 * | 12/2011 | Mintz et al. | 606/4 |
| 2013/0035551 A1 * | 2/2013 | Yu et al. | 600/141 |

FOREIGN PATENT DOCUMENTS

| | | |
|---|---|---|
| JP | A-5-341158 | 12/1993 |
| JP | A-2002-521713 | 7/2002 |
| JP | A-2003-210400 | 7/2003 |
| JP | 2004354782 A * | 12/2004 |
| JP | A-2004-354782 | 12/2004 |
| JP | A-2008-511871 | 4/2008 |
| JP | A-2012-88495 | 5/2012 |

* cited by examiner

FIBER UNIT

CROSS-REFERENCE TO RELATED APPLICATIONS

This application is a continuation of PCT international application Ser. No. PCT/JP2013/063168 filed on May 10, 2013 which designates the United States, incorporated herein by reference, and which claims the benefit of priority from U.S. provisional application No. 61/680,884, filed on Aug. 8, 2012, incorporated herein by reference.

BACKGROUND OF THE INVENTION

1. Field of the Invention

The present invention relates to a fiber unit used in a measurement probe that emits irradiation light to a sample and receives light from the sample.

2. Description of the Related Art

Conventionally, an optical measurement system has been known, which emits illumination light onto a sample such as a biological tissue and estimates characteristics of the sample on the basis of a measurement value of detected light reflected or scattered by the sample. Such an optical measurement system is constituted using: a light source emitting illumination light to a sample; an optical measurement apparatus having a detection unit detecting detected light from the sample; and a measurement probe, which is attachable to and detachable from the optical measurement apparatus, emits irradiation light to the sample, and receives light from the sample.

The measurement probe has a fiber unit including: an illumination fiber, one end of which is connected to a light source and the other end of which emits illumination light to a biological tissue; and a light receiving fiber, one end of which is connected to the detection unit and the other end of which receives light emitted from the biological tissue by emission from the emission fiber.

In such an optical measurement system, LEBS (low-coherence enhanced backscattering) for detecting characteristics of a biological tissue by: emitting, from an end of an illumination fiber of a measurement probe, low-coherence white light having a short spatial coherence length, to the biological tissue; and measuring intensity distributions of scattered light beams of different angles using a plurality of light receiving fibers.

Decrease in a diameter of the measurement probe is demanded in order to reduce burden placed on a patient upon insertion of the measurement probe inside the patient's body. For this demand, a diameter of each fiber of a fiber unit is required to be also decreased.

As a technique for decreasing the diameter of the fiber unit, Japanese Laid-open Patent Publication No. 5-341158 discloses a technique in which a receiving end portion of each fiber is bent to narrow a distance between the fibers, thereby decreasing the diameter, for example.

SUMMARY OF THE INVENTION

A fiber unit according to one aspect of the invention has one or a plurality of illumination fibers and a plurality of detection fibers and is provided in a measurement probe that performs optical measurement by inputting and outputting light from a distal end thereof. Each of the illumination fibers and the detection fibers includes: a soft portion that is bendable; a distal end hard portion provided at an end thereof and having a greater hardness than the soft portion; and a pitch conversion portion that connects the soft portion and the distal end hard portion and changes a distance between adjacent fibers at the distal end hard portion with respect to a distance between the adjacent fibers at the soft portion, by bending and extending. When a most inclined angle of angles each formed by a central axis of the distal end hard portion and a line segment connecting an end portion of the pitch conversion portion closer to the soft portion and an end portion of the pitch conversion portion closer the distal end hard portion is denoted by Deg_max, the following is satisfied: 1.0 degree<Deg_max<6.0 degrees.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
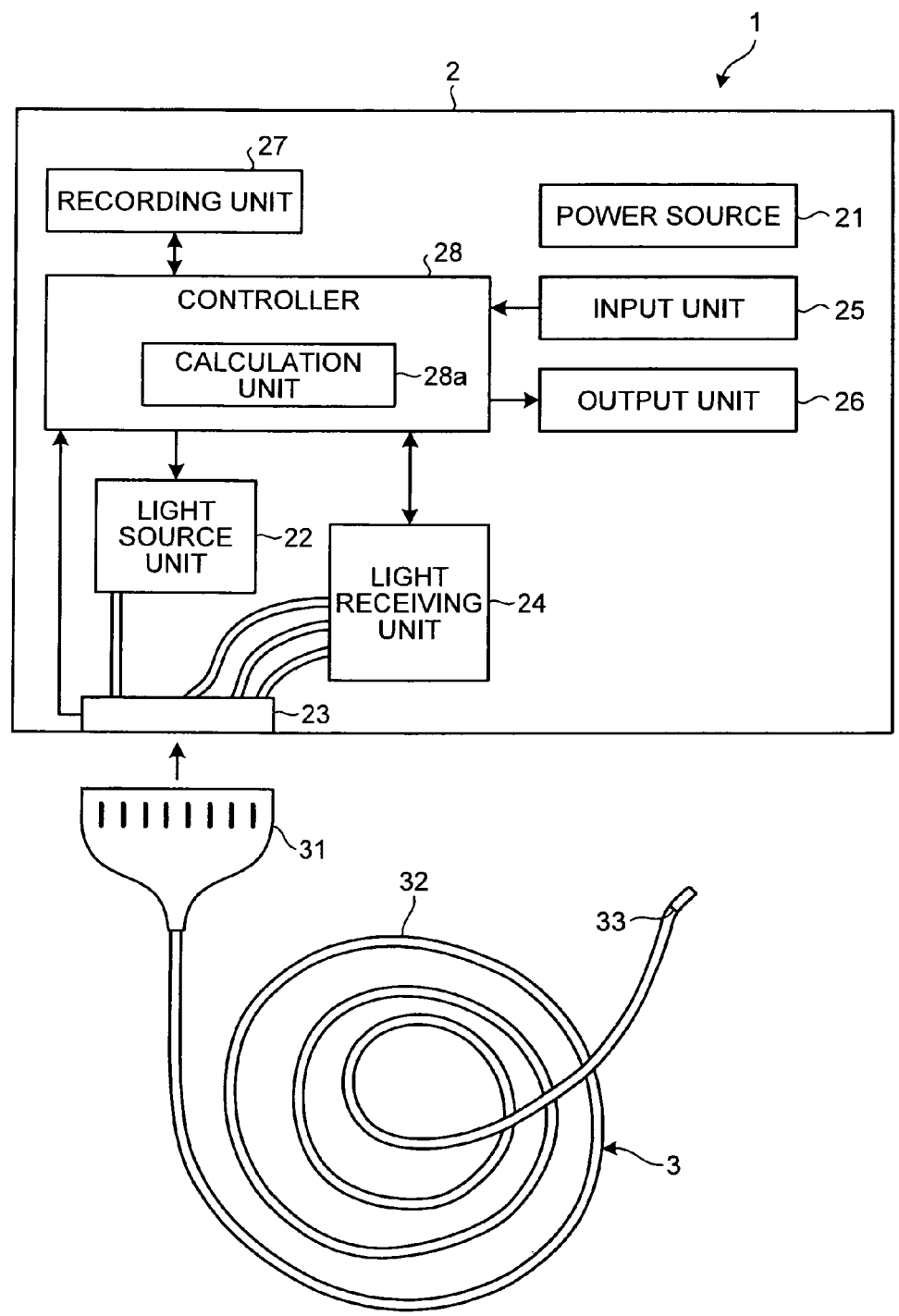
FIG. 1 is a block diagram schematically illustrating a configuration of an optical measurement system according to an embodiment of the present invention.

Hereinafter, a preferred embodiment of a fiber unit according to the present invention will be described in detail with reference to the drawings. The present invention is not limited by this embodiment. In the description of the drawings, like reference numerals denote like elements. Further, it is to be noted that the drawings are schematic, and relations between thicknesses and widths of each element, and ratios among elements are different from those of the actual. Among the drawings also, a same portion having relations or ratios of dimensions different from one another is included. In the explanation below, reference will be made to an optical measurement system as an example of a configuration using a fiber unit.

FIG. 1 is a block diagram schematically illustrating a configuration of an optical measurement system according to an embodiment of the present invention. An optical measurement system 1 illustrated in FIG. 1 includes: an optical measurement apparatus 2 that performs optical measurement with respect to an object to be measured, such as a biological tissue, which is a scatterer, and detects characteristics (properties) of the object to be measured; and a measurement probe 3 which is attachable to and detachable from the optical measurement apparatus 2 and inserted into a subject.

First, the optical measurement apparatus 2 will be explained. The optical measurement apparatus 2 includes a power source 21, a light source unit 22, a connection unit 23, a light receiving unit 24, an input unit 25, an output unit 26, a recording unit 27, and a controller 28. The power source 21 supplies electric power to each component of the optical measurement apparatus 2.

The light source unit 22 is realized using an incoherent light source such as a white LED (light emitting diode), a xenon lamp, a tungsten lamp, or a halogen lamp, and, as necessary, one or more lenses, e.g., a condenser lens, a collimation lens, or the like. The light source unit 22 outputs, to the measurement probe 3, incoherent light having at least one spectrum component to be irradiated onto the object to be measured via the connection unit 23.

The connection unit 23 detachably connects a connector unit 31 of the measurement probe 3 to the optical measurement apparatus 2. The connection unit 23 outputs the light emitted by the light source unit 22 to the measurement probe 3, and outputs, to the light receiving unit 24, returned light of illumination light, which is emitted by the measurement probe 3 and reflected and/or scattered by the object to be measured. The connection unit 23 outputs, to the controller 28, information about whether the measurement probe 3 is connected or not.

The light receiving unit 24 receives and measures the returned light of the illumination light, which is the illumination light emitted from the measurement probe 3 and reflected and/or scattered by the object to be measured. The light receiving unit 24 is realized using a plurality of spectrometric devices or light receiving sensors. More specifically, in the light receiving unit 24, the spectrometric devices are provided according to the number of light receiving fibers of the measurement probe 3 explained later. The light receiving unit 24 measures spectrum components and intensity distribution of the scattered light entering from the measurement probe 3, and performs measurement for each wavelength. The light receiving unit 24 outputs results of the measurement to the controller 28.

The input unit 25 is realized using a push-type switch, a touch panel, or the like, receives input of an instruction signal instructing activation of the optical measurement apparatus 2 or an instruction signal instructing any of other various kinds of operations, and outputs the instruction signal to the controller 28.

The output unit 26 is realized using a display of liquid crystal or organic EL (electroluminescence) and a speaker or the like, and outputs information about various kinds of processing in the optical measurement apparatus 2. Further, under control by the controller 28, the output unit 26 displays on the display numerical values such as intensities of light received by the light receiving unit 24 (characteristics values calculated by an calculation unit 28a explained later).

The recording unit 27 is realized using a volatile memory and a nonvolatile memory, and records various kinds of programs for operating the optical measurement apparatus 2, and various kinds of data and various kinds of parameters used for optical measurement processing. The recording unit 27 temporarily records information during processing of the optical measurement apparatus 2. The recording unit 27 records results of measurement by the optical measurement apparatus 2 in association with a subject to be measured. The recording unit 27 may be configured using a memory card or the like, which is attached from the outside of the optical measurement apparatus 2.

The controller 28 is configured using a CPU (central processing unit) or the like. The controller 28 controls processing operations of each unit of the optical measurement apparatus 2. The controller 28 controls operations of the optical measurement apparatus 2 by, e.g., transferring instruction information and data corresponding to each unit of the optical measurement apparatus 2. The controller 28 records the results of the measurement by the light receiving unit 24 in the recording unit 27. The controller 28 has a calculation unit 28a.

The calculation unit 28a performs, on the basis of the results of the measurement by the light receiving unit 24, a plurality of operation processes, and calculates characteristic values related to the characteristics of the object to be measured. A type of these characteristics values is set, for example, according to an instruction signal received by the input unit 25.

Subsequently, the measurement probe 3 will be explained. The measurement probe 3 is realized by arranging a plurality of optical fibers inside. More specifically, the measurement probe 3 is realized using an illumination fiber that emits illumination light onto the object to be measured and a plurality of light receiving fibers into which returned light of the illumination light reflected and/or scattered by the object to be measured enters at different angles. The measurement probe 3 includes: a connector unit 31 detachably connected to the connection unit 23 of the optical measurement apparatus 2; a flexible unit 32 having flexibility; and a distal end portion 33 which irradiates the illumination light supplied by the light source unit 22 and receives the returned light from the object to be measured.

Figure 2:
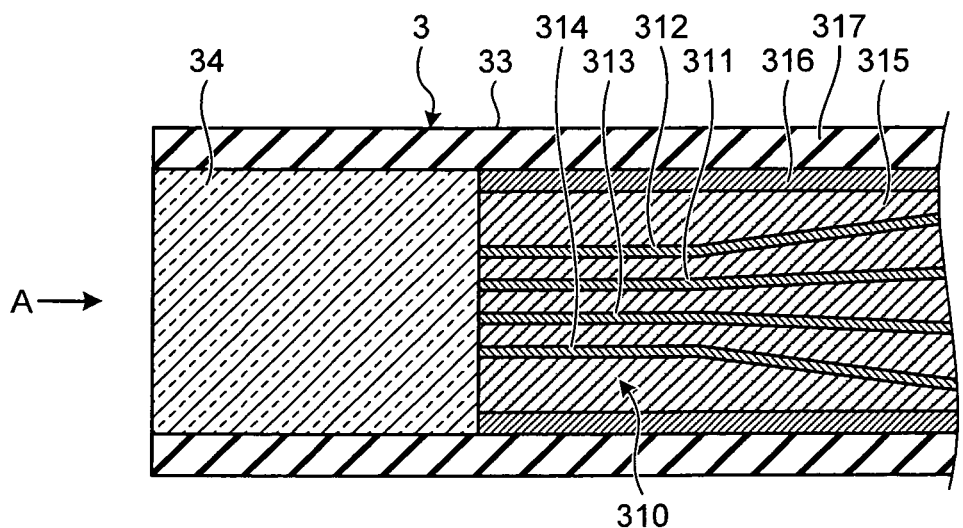
FIG. 2 is a diagram schematically illustrating a cross section of a distal end portion of a measurement probe including an optical element of the optical measurement system according to the embodiment of the present invention, cut along a longitudinal direction.
Figure 3:
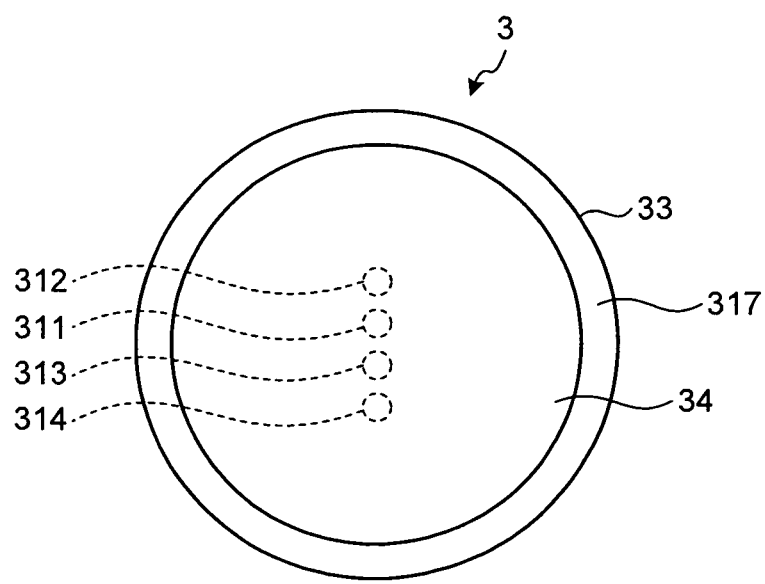
FIG. 3 is a plan view schematically illustrating a measurement probe in a direction of arrow A of FIG. 2.

The configuration of the distal end portion 33 of the measurement probe 3 will be explained in detail. FIG. 2 is a diagram schematically illustrating a cross section of the distal end portion 33 of the measurement probe 3 cut along a longitudinal direction. FIG. 3 is a plan view schematically illustrating the measurement probe 3 in a direction of arrow A of FIG. 2. As illustrated in FIG. 2, the distal end portion 33 is provided with an optical element 34 partly constituting an external surface of the measurement probe 3.

The measurement probe 3 includes: a fiber unit 310 including an illumination fiber 311 that irradiates the illumination light onto the object to be measured, and a first light receiving fiber 312, a second light receiving fiber 313, and a third light receiving fiber 314, into which the returned light of the illumination light reflected and/or scattered by the object to be measured enters; a covering member 315 of glass, resin, or the like, which prevents scratches on and fixes positions of the illumination fiber 311, the first light receiving fiber 312, the second light receiving fiber 313, and the third light receiving fiber 314; a protection unit 316 of glass, brass, or the like, which protects the covering member 315 from external force; and a probe outer cover 317 made of SUS or the like, which covers an external peripheral surface of the protection unit 316 and the optical element 34.

The illumination fiber 311 transmits the illumination light output from the light source unit 22 and irradiates the illumination light onto the object to be measured via the optical element 34. The number of illumination fibers 311 may be changed as necessary according to an item to be examined or the type of the object to be measured, e.g., a bloodstream or a locus. For example, the illumination fiber 311 is configured using a step-index-type single-core fiber.

The first light receiving fiber 312, the second light receiving fiber 313, and the third light receiving fiber 314 transmit the returned light of the illumination light reflected and/or scattered by the object to be measured and entering from their respective distal ends via the optical element 34, and output it to the light receiving unit 24 of the optical measurement apparatus 2. The number of light receiving fibers may be changed as necessary according to the item to be examined or the type of the object to be measured, e.g., a bloodstream or a locus. For example, the first light receiving fiber 312, the second light receiving fiber 313, and the third light receiving fiber 314 are configured using step-index-type single-core fibers.

The optical element 34 is cylindrically shaped, and is configured using transparent glass having a predetermined refractive index. The optical element 34 fixes a distance between the illumination fiber 311 and the object to be measured, and is formed to be able to emit light with a constant spatial coherent length. In addition, the optical element 34 fixes each of a distance between the first light receiving fiber 312 and the object to be measured, a distance between the second light receiving fiber 313 and the object to be measured, and a distance between the third light receiving fiber 314 and the object to be measured, and is formed to be able to stably receive the returned light at a predetermined scattering angle.

Figure 4:
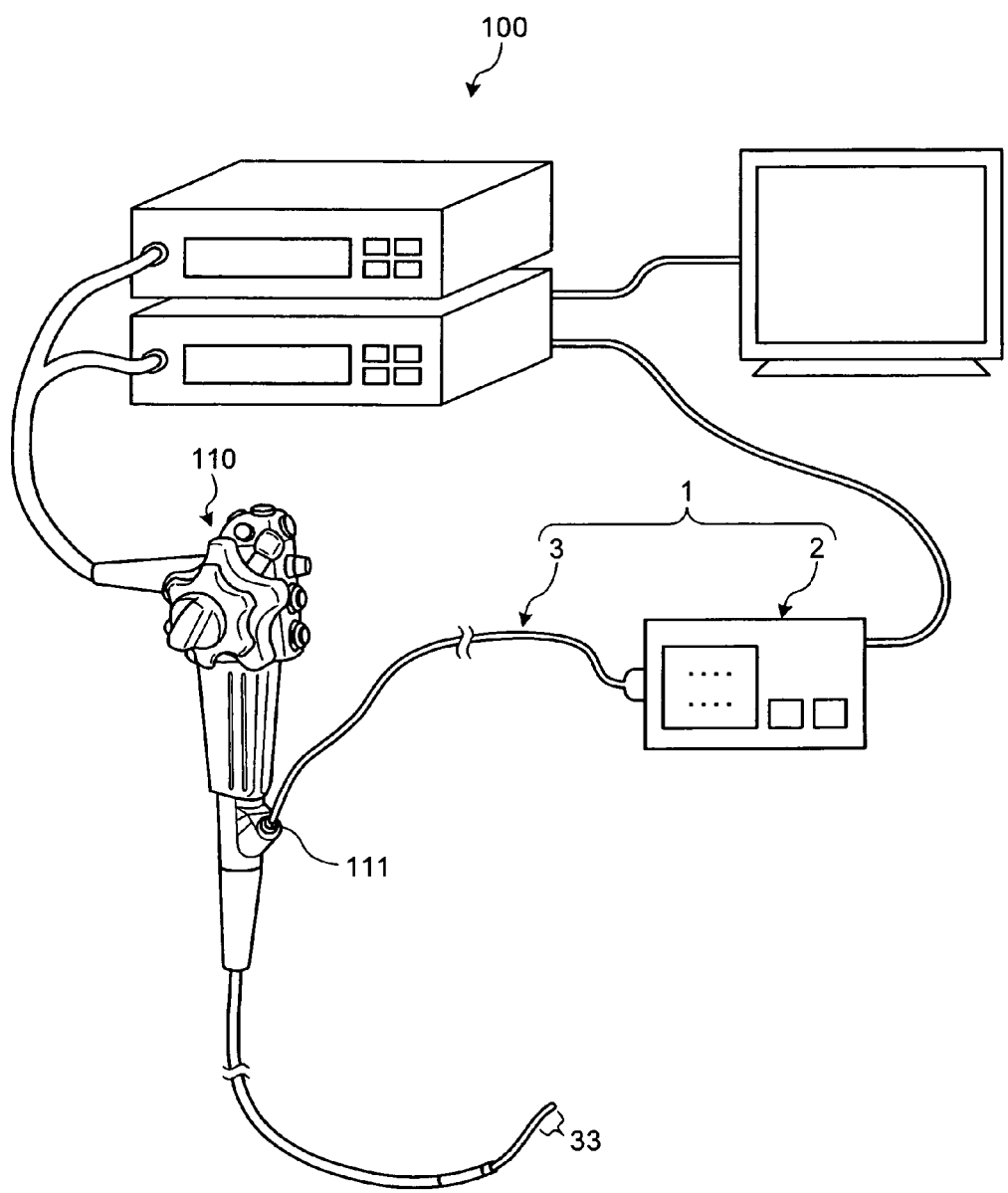
FIG. 4 is a diagram illustrating the optical measurement system according to the embodiment of the present invention upon use in an endoscopic system.

As illustrated in FIG. 4, in the optical measurement system 1 configured as described above, the measurement probe 3 is inserted into the subject via a treatment tool channel 111 provided in an endoscopic apparatus 110 (endoscope) of an endoscopic system 100, and the illumination fiber 311 irradiates the illumination light onto the object to be measured, and the first light receiving fiber 312, the second light receiving fiber 313, and the third light receiving fiber 314 respectively receive the returned light beams of the illumination light reflected and/or scattered by the object to be measured at different scattering angles, and transmit them to the light receiving unit 24 of the optical measurement apparatus 2. Thereafter, the calculation unit 28a calculates characteristic values for the characteristics of the object to be measured on the basis of the results of the measurement by the light receiving unit 24.

Herein, the illumination fiber 311, the first light receiving fiber 312, the second light receiving fiber 313, and the third light receiving fiber 314 of the measurement probe 3 are bent so that distances between adjacent fibers at the distal end portion 33 are shortened, and are in contact with the optical element 34.

Figure 5:
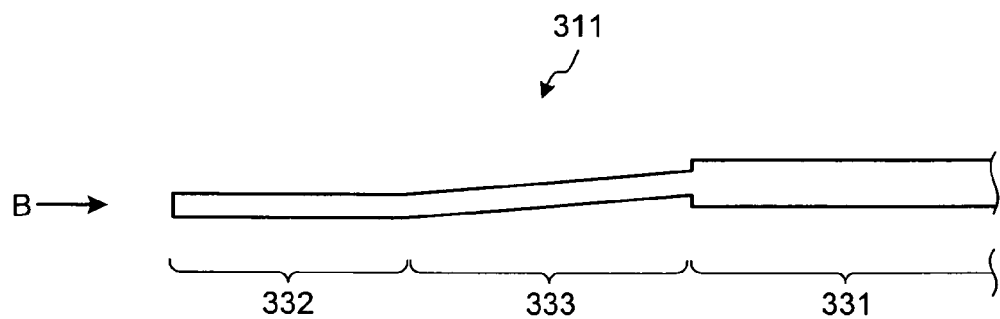
FIG. 5 is a schematic diagram illustrating a configuration of an emission fiber of the optical measurement system according to the embodiment of the present invention.
Figure 6:
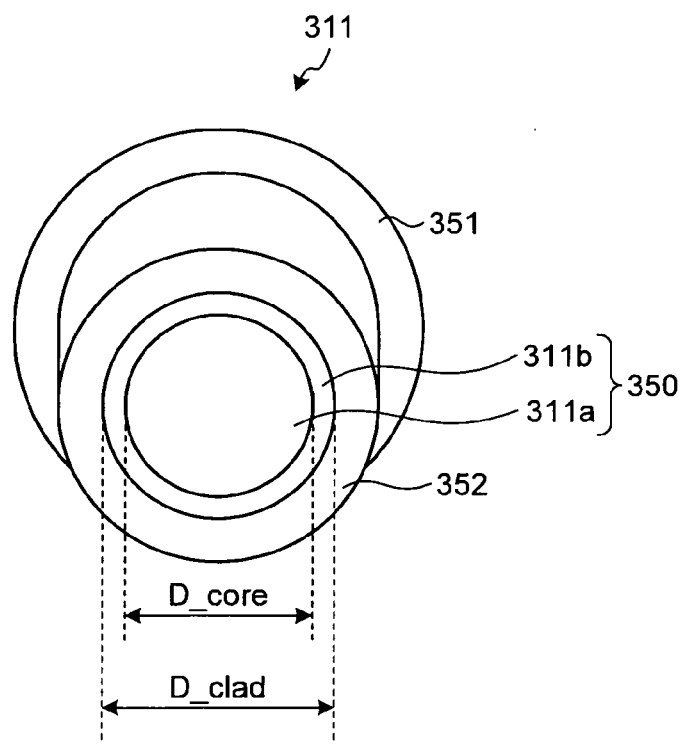
FIG. 6 is a plan view schematically illustrating the emission fiber in a direction of arrow B of FIG. 5.
Figure 7:
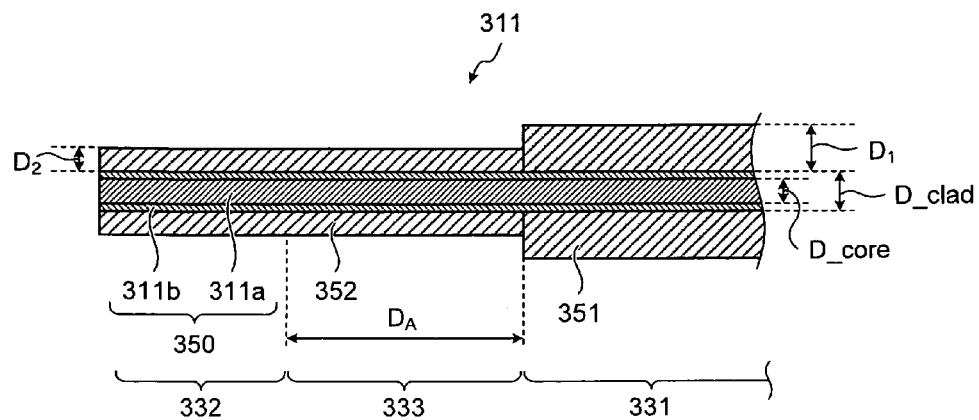
FIG. 7 is a cross sectional view schematically illustrating a configuration of the emission fiber of the optical measurement system according to the embodiment of the present invention.

FIG. 5 is a schematic diagram illustrating a configuration of the emission fiber 311 of the optical measurement system 1 according to the present embodiment. FIG. 6 is a plan view schematically illustrating the emission fiber 311 in a direction of arrow B of FIG. 5. FIG. 7 is a cross sectional view schematically illustrating a configuration of the emission fiber 311 of the optical measurement system 1 according to the present embodiment.

As illustrated in FIG. 5, the illumination fiber 311 includes a soft portion 331 which is inserted into the flexible unit 32 and which is bendable, a distal end hard portion 332 which is a light-receiving end portion and has a hardness greater than the soft portion 331, and a pitch conversion portion 333 which connects the soft portion 331 and the end hard portion 332 and changes a distance (pitch) from another fiber adjacent thereto at the distal end hard portion 332 with respect to a distance between adjacent fibers at the soft portion 331, by bending and extending at both ends thereof. The first light receiving fiber 312, the second light receiving fiber 313, and the third light receiving fiber 314 also have the same configuration.

The pitch conversion portion 333 connects the soft portion 331 and the end hard portion 332 in such a way that a line through a central axis of the soft portion 331 does not coincide with a line though a central axis of the end hard portion 332. The pitch conversion portion 333 may be straight-lined, for example, inclined with respect to the central axis of the soft portion 331, and extended. Alternatively, the pitch conversion portion 333 may be arc-shaped so that the line through the central axis of the soft portion 331 does not coincide with the line though the central axis of the end hard portion 332. As for a fiber located at a center of the fiber unit 310 (covering member 315), a line through a central axis of the soft portion 331 may coincide with a line though a central axis of the end hard portion 332.

In this pitch conversion portion 333, if an inclination angle of the most inclined fiber of the first light receiving fiber 312, the second light receiving fiber 313, and the third light receiving fiber 314 is denoted by Deg_max, the inclination angle Deg_max for preventing fiber breakage satisfies the following conditional expression. The present embodiment is described assuming that the pitch conversion portion 333 is straight-lined, and the inclination angle is an angle formed by the pitch conversion portion 333 and a central axis of the distal end hard portion 332.

$$1.0 \text{ degree} < \text{Deg\_max} < 6.0 \text{ degrees} \tag{1}$$

As illustrated in FIGS. 6 and 7, the illumination fiber 311 includes: a light transmission unit 350 including a core unit 311a (core), which transmits light and is approximately bar-shaped, and an outer layer unit 311b (clad), which covers an external periphery of the core unit 311a and has a smaller refractive index than the core unit 311a; a first covering unit 351 covering a lateral surface of the outer layer unit 311b of the soft portion 331 of the illumination fiber 311; and a second covering unit 352, which is provided at the light-receiving end of the illumination fiber 311 (the distal end hard portion 332 and the pitch conversion portion 333) and covers the lateral surface of the outer layer unit 311b. The lateral surface of the outer layer unit 311b is covered with the first covering unit 351 and the second covering unit 352. A covering thickness $D_1$ of the outer layer unit 311b of the first covering unit 351 is different from a covering thickness $D_2$ of the outer layer unit 311b of the second covering unit 352, and satisfies a relation, $D_2 < D_1$.

The first light receiving fiber 312, the second light receiving fiber 313, and the third light receiving fiber 314 also have the same configuration. In the light transmission unit 350, the refractive index of the core unit 311a is greater than the refractive index of the outer layer unit 311b, and therefore, light is mainly transmitted by the core unit 311a.

At the inclination angle Deg_max, a length $D_A$ of the pitch conversion portion 333 with respect to the covering thickness $D_1$ for preventing fiber breakage satisfies the following conditional expression. The length $D_A$ of the pitch conversion portion is a length ( ) along a longitudinal direction of the distal end hard portion 332 (the central axis of the fiber).

$$0.005 < D_1/D_A < 0.032 \tag{2}$$

At the inclination angle Deg_max, the covering thicknesses $D_1$ and $D_2$ for preventing fiber breakage satisfy the following conditional expression.

$$15 < D_1/D_2 < 100 \tag{3}$$

Because LEBS performed in the optical measurement system 1 is a diagnostic method using interference light, it is necessary to keep a constant spatial coherent length of the light irradiated onto the object to be measured in order to reduce the diameter of the measurement probe 3 without changing the diagnostic method. For this reason, the illumination fiber 311, the first light receiving fiber 312, the second light receiving fiber 313, and the third light receiving fiber 314 satisfy the following conditional expressions.

$$0.20 < NA < 0.25 \qquad (4)$$

$$15\ \mu m < D\_core < 45\ \mu m \qquad (5)$$

$$0.60 < D\_core/D\_clad < 0.75 \qquad (6)$$

NA denotes a numerical aperture of each of the illumination fiber 311 and the first light receiving fiber 312 to third light receiving fiber 314. D_core denotes a core diameter of the core unit 311a of each of the illumination fiber 311 and first light receiving fiber 312 to third light receiving fiber 314. D_clad is a clad diameter of the outer layer unit 311b of each of the illumination fiber 311 and the first light receiving fiber 312 to third light receiving fiber 314.

When the core diameter D_core of the core unit 311a is within the range of 15 μm<D_core<45 μm, a distance between centers of the core units 311a of the fibers are reducible while an appropriate quantity of light is able to be input and output.

Further, when the core diameter D_core of the core unit 311a and the clad diameter D_clad of the outer layer unit 311b satisfy the relation of 0.60<D_core/D_clad<0.75, it is possible to suppress increase in a diameter of the light transmission unit 350 while preventing the light transmitted by the core unit 311a from leaking out of the outer layer unit 311b.

According to the present embodiment explained above, of the fibers each having the soft portion 331, the distal end hard portion 332, and the pitch conversion portion 333, the inclination angle Deg_max of the pitch conversion portion 333 of the most inclined fiber satisfies 1.0 degree<Deg_max<6.0 degrees, and therefore, fiber breakage upon manufacture is preventable.

More specifically, by the inclination angle Deg_max satisfying Deg_max<6.0 degrees, fiber breakage is prevented, and by satisfying 1.0 degree<Deg_max, the pitch conversion portion 333 is prevented from being longer than necessary.

Further, according to the present embodiment, at the inclination angle Deg_max, the length $D_A$ of the pitch conversion portion 333 with respect to the covering thickness $D_1$ satisfies the relation of 0.005<$D_1/D_A$<0.032, and therefore, the covering thickness $D_1$ of the first covering unit 351 with respect to the length of the pitch conversion portion 333 becomes an appropriate ratio, and the inclination angle Deg_max of the pitch conversion portion 333 is able to satisfy 1.0 degree<Deg_max<6.0 degrees.

For example, when $D_1/D_A$<0.005, a gap is generated between the first covering units 351 of the fibers if the inclination angle Deg_max of the pitch conversion portion 333 is within the range of 1.0 degree<Deg_max<6.0 degrees. When 0.032<$D_1/D_A$, the distance between the centers of the fibers increases, and therefore, even if the first covering units 351 are arranged to be in contact with each other, the inclination angle Deg_max becomes greater than 6.0 degrees.

According to the present embodiment, the covering thicknesses $D_1$ and $D_2$ are adapted to satisfy the relation of 15<$D_1/D_2$<100, and therefore, it is possible to even more reliably prevent fiber breakage while the inclination angle Deg_max and the ratio $D_1/D_A$ between the first covering unit 351 and the second covering unit 352 are being satisfied.

The present embodiment has been explained assuming that the pitch conversion portion 333 is straight-lined. If the pitch conversion portion 333 is arc-shaped, the inclination angle is an angle formed by the central axis of the distal end hard portion 332 and a line segment connecting an end portion of the pitch conversion portion 333 closer to the soft portion 331 and an end portion of the pitch conversion portion 333 closer to the distal end hard portion 332, and the maximum angle thereof is the inclination angle Deg_max.

Further, the present embodiment has been explained assuming that the first covering unit 351 and the second covering unit 352 are provided for the outer layer unit 311b of the fiber, but as long as the above conditional expressions (1) to (6) are satisfied, a configuration thereof may be without the second covering unit 352.

Further, the present embodiment has been explained assuming that only one illumination fiber 311 is provided in the measurement probe 3, but a configuration thereof may be provided with a plurality of illumination fibers.

In the conditional expression (1), the following is preferable.

$$1.5\ degrees < Deg\_max < 5.5\ degrees \qquad (1)'$$

Further, in the conditional expression (3), the following is preferable.

$$20 < D_1/D_2 < 80 \qquad (3)'$$

And the following is more preferable.

$$24 < D_1/D_2 < 63 \qquad (3)''$$

Further, in the conditional expression (4), the following is preferable.

$$0.21 < NA < 0.23 \qquad (4)'$$

Further, in the conditional expression (5), the following expression is preferable.

$$20\ \mu m < D\_core < 30\ \mu m \qquad (5)'$$

And, the following is more preferable.

$$23\ \mu m < D\_core < 27\ \mu m \qquad (5)''$$

Further, in the conditional expression (6), the following is preferable.

$$0.70 < D\_core/D\_clad < 0.73 \qquad (6)'$$

EXAMPLES

Hereinafter, the present invention will be explained more specifically by way of examples, but the present invention is not limited by these. Measurement probes having fibers satisfying the above conditional expressions were respectively made as examples 1 to 3. Fiber units below, as described in the above embodiment, each include one emission fiber and three light receiving fibers, and the emission fiber and the light receiving fibers are arranged in a line at equal intervals. A center of the arranged fiber unit coincides with a center of the fibers.

Example 1

A measurement probe having fibers satisfying the following conditions was made. Nickel plating or gold plating was used for the first covering unit 351. Acrylic resin was used for the second covering unit 352.

Covering thickness $D_1$ of the outer layer unit 311b of the first covering unit 351:

$$D_1 = 63\ \mu m$$

Covering, thickness $D_2$ of the outer layer unit 311b of the second covering unit 352:

$D_2$=1 µm

Length $D_A$ of the pitch conversion portion 333:

$D_A$=2.0 mm $D_1/D_A$ (conditional expression (2)):

$D_1/D_A$=0.0315

$D_1/D_2$ (conditional expression (3)):

$D_1/D_2$=63

Numerical aperture NA (conditional expression (4)):

NA=0.22

Core diameter D_core of the core unit 311a (conditional expression (5)):

D_core=25 µm

Clad diameter D_clad of the outer layer unit 311b:

D_clad=34 µm

Core diameter D_core/clad diameter D_clad (conditional expression (6)):

D_core/D_clad≈0.74

Figure 8:
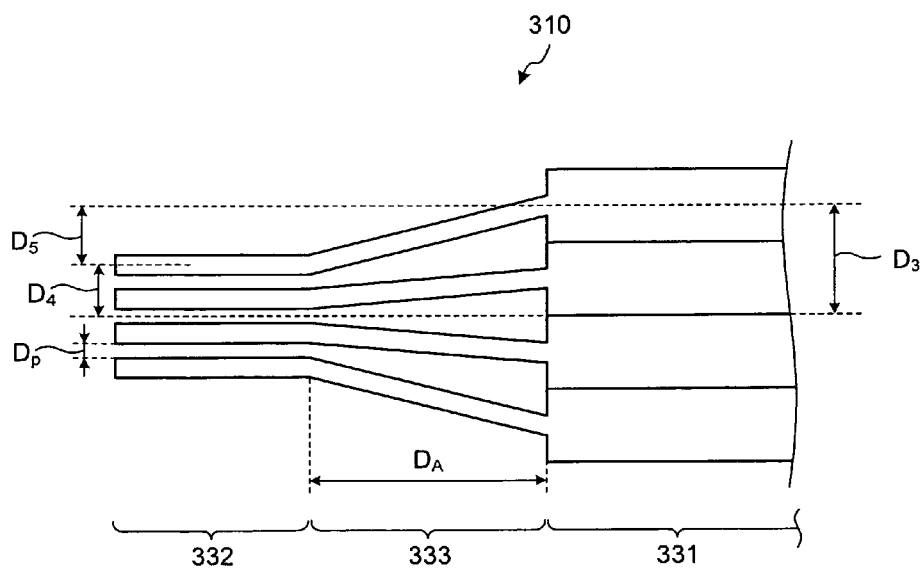
FIG. 8 is a diagram illustrating distances between fibers of a fiber unit according to examples of the present invention.

In the fiber unit according to the example 1, when the longitudinal direction of the soft portion 331 and the longitudinal direction of the end hard portion 332 are arranged in parallel with each other, the soft portions 331 of the respective fibers are in contact with one another, and an interval $D_P$ between the distal end hard portions 332 is 2 µm (see FIG. 8), the following holds.

Diameter (µm) of the distal end hard portion 332:

D_clad(clad diameter)+$D_2$ (covering thickness)×
2=34+1×2=36 (µm)

Distance $D_3$ (µm) from the center of the fiber unit to the center of the outermost soft portion 331:

$$D_3 = (D\_clad + D_1 (\text{covering thickness}) \times 2) \times 1.5$$
$$= (34 + 63 + 2) \times 1.5$$
$$= 243 (\mu m)$$

Distance $D_4$ (µm) from the center of the fiber unit to the center of the outermost distal end hard portion 332:

$$D_4 = (\text{diameter of end hard portion } 332 \times 1.5) + D_P \times 1.5$$
$$= (36 \times 1.5) + 2 \times 1.5$$
$$= 57 (\mu m)$$

Distance $D_5$ between the center of the outermost soft portion 331 and the center of the distal end hard portion 332:

$D_5$=$D_3$−$D_4$=243−57=186 (µm)

From the length $D_A$ of the pitch conversion portion 333 and the distance $D_5$, the inclination angle Deg_max of the pitch conversion portion 333 with respect to the longitudinal direction of the distal end hard portion 332 (conditional expression (1)) becomes:

$$\text{Deg\_max} = \text{Atan}(D_5 / D_A)$$
$$= \text{Atan}(0.186 / 2.0)$$
$$\approx 5.31 (\text{degrees})$$

Example 2

A measurement probe having fibers satisfying the following conditions was made. Nickel plating or gold plating was used for the first covering unit 351. Acrylic resin was used for the second covering unit 352.

Covering thickness $D_1$ of the outer layer unit 311b of the first covering unit 351:

$D_1$=48 µm

Covering thickness $D_2$ of the outer layer unit 311b of the second covering unit 352:

$D_2$=2 µm

Length $D_A$ of the pitch conversion portion 333:

$D_A$=6.00 mm $D_1/D_A$(conditional expression (2)):

$D_1/D_A$=0.008

$D_1/D_2$(conditional expression (3)):

$D_1/D_2$=24

Numerical aperture NA (conditional expression (4)):

NA=0.224

Core diameter D_core of the core unit 311a (conditional expression (5)):

D_core=21 µm

Clad diameter D_clad of the outer layer unit 311b:

D_clad=30 µm

Core diameter D_core/clad diameter D_clad (conditional expression (6)):

D_core/D_clad=0.70

Like the example 1, in the fiber unit according to the example 2, when the longitudinal direction of the soft portion 331 and the longitudinal direction of the distal end hard portion 332 are arranged in parallel with each other, the soft portions 331 of the respective fibers are caused to be in contact with each other, and an interval $D_P$ between the distal end hard portions 332 is 2 µm (see FIG. 8), the following holds.

Diameter of the distal end hard portion 332 (µm):

D_clad(clad diameter)+$D_2$ (covering thickness)×
2=30+2×2=34 (µm)

Distance $D_3$ (µm) from the center of the fiber unit to the center of the outermost soft portion 331:

$$D_3 = (D\_clad + D_1 (\text{covering thickness}) \times 2) \times 1.5$$
$$= (30 + 48 \times 2) \times 1.5$$
$$= 189 (\mu m)$$

Distance $D_4$ from the center of the fiber unit to the center of the outermost distal end hard portion 332 (µm):

$$D_4 = \text{(diameter of end hard portion } 332 \times 1.5) + D_P \times 1.5$$
$$= (34 \times 1.5) + 2 \times 1.5$$
$$= 54 (\mu m)$$

Distance $D_5$ between the center of the outermost soft portion 331 and the center of the distal end hard portion 332:

$$D_5 = D_3 - D_4 = 189 - 54 = 135 \; (\mu m)$$

From the length $D_A$ of the pitch conversion portion 333 and the distance $D_5$, the inclination angle Deg_max of the pitch conversion portion 333 with respect to the longitudinal direction of the distal end hard portion 332 (conditional expression (1)) becomes:

$$\text{Deg\_max} = \text{Atan}(D_5/D_A)$$
$$= \text{Atan}(0.135/6.0)$$
$$\approx 1.3 \text{(degrees)}$$

Example 3

A measurement probe having fibers satisfying the following conditions was made. Each fiber according to the example 3 was not provided with the first covering unit 351, and acrylic resin was used for the second covering unit 352.
Covering thickness $D_1$ of the outer layer unit 311b of the first covering unit 351:

$$D_1 = 54 \; \mu m$$

Covering thickness $D_2$ of the outer layer unit 311b of the second covering unit 352:

$$D_2 = 0 \; \mu m$$

Length $D_A$ of the pitch conversion portion 333:

$$D_A = 4.5 \text{ mm}$$

$D_1/D_A$ (conditional expression (2)):

$$D_1/D_A = 0.012$$

$D_1/D_2$ (conditional expression (3)): no numerical value
Numerical aperture NA (conditional expression (4)):

$$NA = 0.222$$

Core diameter D_core of the core unit 311a (conditional expression (5)):

$$D\_core = 26 \; \mu m$$

Clad diameter D_clad of the outer layer unit 311b:

$$D\_clad = 36 \; \mu m$$

Core diameter D_core/clad diameter D_clad (conditional expression (6)):

$$D\_core/D\_clad = 0.72$$

Like the example 1, in the fiber unit according to the example 3, when the longitudinal direction of the soft portion 331 and the longitudinal direction of the distal end hard portion 332 are arranged in parallel with each other, the soft portions 331 of the respective fibers are in contact with one another, and an interval $D_P$ between the end hard portions 332 is 2 μm (see FIG. 8), the following holds.

Diameter (μm) of end hard portion 332:

$$D\_clad \text{(clad diameter)} = 36 \; (\mu m)$$

Distance $D_3$ (μm) from the center of the fiber unit to the center of the outermost soft portion 331:

$$D_3 = (D\_clad + D_1 \text{(covering thickness)} \times 2) \times 1.5$$
$$= (36 + 54 \times 2) \times 1.5$$
$$= 216 (\mu m)$$

Distance $D_4$ (μm) from the center of the fiber unit to the center of the outermost distal end hard portion 332:

$$D_4 = \text{(diameter of end hard portion } 332 \times 1.5) + D_P \times 1.5$$
$$= (36 \times 1.5) + 2 \times 1.5$$
$$= 57 (\mu m)$$

Distance $D_5$ between the center of the outermost soft portion 331 and the center of the end hard portion 332:

$$D_5 = D_3 - D_4 = 216 - 57 = 159 \; (\mu m)$$

From the length $D_A$ of the pitch conversion portion 333 and the distance $D_5$, the inclination angle Deg_max of the pitch conversion portion 333 with respect to the longitudinal direction of the end hard portion 332 (conditional expression (1)) becomes:

$$\text{Deg\_max} = \text{Atan}(D_5/D_A)$$
$$= \text{Atan}(0.159/4.5)$$
$$\approx 2.0 \text{(degrees)}$$

Upon manufacture of the measurement probes according to the above examples 1 to 3, when the fiber units having the fibers satisfying the above conditions (1) to (6) were assembled, the measurement probes were able to be manufactured without fiber breakage caused by contact or the like. Furthermore, when a fiber unit that is out of the ranges of the above conditional expressions was used and assembled, some of the fibers were broken due to contact or the like.

As described above, the fiber unit according to the present invention is useful in preventing the fiber breakage upon manufacture.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A fiber unit having one or a plurality of illumination fibers and a plurality of detection fibers and provided in a measurement probe that performs optical measurement by inputting and outputting light from a distal end thereof, wherein each of the illumination fibers and the detection fibers comprises:
   a soft portion that is bendable;
   a distal end hard portion having a greater hardness than the soft portion; and a pitch conversion portion that connects the soft portion and the distal end hard portion of each fiber and is bendable and extendable, wherein:
    the distal end hard portion has a central axis in a length direction thereof;
    the pitch conversion portion comprises:
        a first end point adjacent to the distal end hard portion; and
        a second end point adjacent to the soft portion;
    a line segment bound by the first end point and the second end point of the pitch conversion portion of each fiber is at an angle to the central axis of the distal end hard portion of each fiber;
    a maximum degree of the angle formed by the line segment and the central axis of the distal end hard portion of each fiber is greater than 1.0 degree and less than 6.0 degrees; and
    a distance between the distal end hard portions of adjacent fibers is different from a distance between the soft portions of the adjacent fibers.

2. The fiber unit according to claim 1, further comprising a first covering unit that covers a lateral surface of the soft portion, wherein:
    the first covering unit has a covering thickness ($D_1$);
    the pitch conversion portion has a length ($D_A$); and
    a ratio of $D_1$ to $D_A$ is greater than 0.005 and less than 0.032.

3. The fiber unit according to claim 2, further comprising a second covering unit that covers lateral surfaces of the distal end hard portion and the pitch conversion portion, wherein:
    the second covering unit has a covering thickness ($D_2$); and
    a ratio of $D_1$ to $D_2$ is greater than 15 and less than 100.

4. The fiber unit according to claim 1, wherein the illumination fibers and the detection fibers are arranged in a line.

5. The fiber unit according to claim 1, wherein each of the illumination fibers and the detection fibers includes a core unit that transmits light, wherein the core unit has a diameter that is greater than 15 μm and less than 45 μm.

6. The fiber unit according to claim 5, wherein each of the illumination fibers and the detection fibers comprises an outer layer unit covering an external periphery of the core unit and having a refractive index smaller than the core unit, wherein:
    a ratio of the diameter of the core unit and a diameter of the outer layer unit is greater than 0.60 and less than 0.75;
    each of the illumination fibers and the detection fibers has a numerical aperture that is greater than 0.20 and less than 0.25.

\* \* \* \* \*